(12) United States Patent
Kamo (10) Patent No.: US 8,647,260 B2
(45) Date of Patent: Feb. 11, 2014

(54) IMAGE APPARATUS FOR ENDOSCOPES (75) Inventor: Yuji Kamo, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1053 days.

(21) Appl. No.: 12/434,464

(22) Filed: May 1, 2009

(65) Prior Publication Data

US 2009/0278920 A1  Nov. 12, 2009

(30) Foreign Application Priority Data

May 12, 2008  (JP) .................................. 2008-124544

(51) Int. Cl.
A61B 1/04 (2006.01)

(52) U.S. Cl.
USPC ............ 600/114; 600/129; 600/173; 600/182

(58) Field of Classification Search
USPC .......... 348/42, 43, 45, 65; 600/114, 129, 173, 600/182
See application file for complete search history.

(56) References Cited

U.S. PATENT DOCUMENTS

| | | | | |
|---|---|---|---|---|
| 4,974,090 A * | 11/1990 | Kawamura et al. | ......... | 348/217.1 |
| 4,980,772 A * | 12/1990 | Kawamura et al. | ......... | 348/217.1 |
| 6,136,410 A * | 10/2000 | Okamoto et al. | ............ | 428/141 |
| 6,368,270 B1 * | 4/2002 | Takami | .......................... | 600/178 |
| 7,318,806 B2 * | 1/2008 | Kohno | .......................... | 600/463 |
| 7,322,934 B2 * | 1/2008 | Miyake et al. | ................ | 600/173 |
| 7,429,242 B2 * | 9/2008 | Kawata | ......................... | 600/109 |
| 8,155,477 B2 * | 4/2012 | Utsugi | .......................... | 382/275 |
| 8,419,620 B2 * | 4/2013 | Segawa et al. | ................ | 600/117 |
| 2005/0272971 A1 * | 12/2005 | Ohnishi et al. | ................ | 600/101 |
| 2007/0014031 A1 * | 1/2007 | Kohno et al. | ................. | 359/687 |
| 2007/0109637 A1 * | 5/2007 | Cook | ............................ | 359/399 |

FOREIGN PATENT DOCUMENTS

| | | |
|---|---|---|
| JP | H06-034891 A | 2/1994 |
| JP | H10-290777 A | 11/1998 |
| JP | H11-252431 A | 9/1999 |
| JP | 2003-333588 A | 11/2003 |
| JP | 2005-279054 A | 10/2005 |

* cited by examiner

Primary Examiner — Lashonda Jacobs (74) Attorney, Agent, or Firm — Arnold International; Bruce Y. Arnold (57) ABSTRACT

The invention relates to an image apparatus for endoscopes, which makes sure easier viewing especially at a peripheral portion of a screen while taking care of the observing angle of view and size of an optical system. The image apparatus comprises an optical system adapted to form an optical image of an object, an image pickup device adapted to convert the formed optical image into electric signals to obtain image data, and an image processing means adapted to move and transform a position of the optical image acquired by the image pickup device. A radiation direction magnification is transformable by the image processing means independently from a concentric direction magnification, and a magnification for a conformal object is higher at a peripheral portion than at a central portion of a screen.

24 Claims, 9 Drawing Sheets

FIG. 1(a)

Inside of the tract and cavity

Correction of distortion

FIG. 1(b)

Lesion

FIG. 2

Entrance pupil position of the optical system

Virtual sphere

Normal mode           Distortion correction mode

FIG. 13(b)

Normal mode           Distortion correction mode Range for optical design

IMAGE APPARATUS FOR ENDOSCOPES

BACKGROUND OF THE INVENTION

The present invention relates generally to an image apparatus for endoscopes, and specifically to an image apparatus for endoscope systems that can be used for obtaining internal views of, for instance, living bodies, laid-down pipes or the like.

Endoscopes are apparatus used widely in the medical and industrial fields. Especially in the medical field, images obtained via an endoscope inserted through the body cavity are used for diagnosis of affected sites. However, the body cavity often have complicated configurations, and especially in the case of a tract and cavity having folds and protuberances, there are sites hard to see, even when the leading end of the endoscope is bent to turn its viewing direction. For instance, when it comes to the large intestine, difficulty is encountered in viewing its whole area because there are large folds whose backs are hard to see.

One possible approach is to have a wide-angle optical system thereby widening the range to be viewed. This would ensure that the leading end of the endoscope is slightly bent to implement a wider range of viewing.

However, the wide-angle optical system is generally likely to produce distortion by which objects on the periphery of a screen are reduced and seen distorted. Although that distortion may be corrected by optical design, there are increases in the number of lenses and lens diameter. This is unsuitable for use with very small apparatus such as endoscopes, imposing some limitations.

Therefore, methods for correction of distortion by image processing have been proposed, as set forth in Patent Publications 1, 2 and 3.

A method for changing the amount of correction of distortion is also set forth in Patent Publication 4.

Patent Publication 1: JP(A) 2005-110207
Patent Publication 2: JP(A) 2007-38856
Patent Publication 3: JP(A) 2007-124088
Patent Publication 4: JP(A) 11-275444

However, these prior arts have the following problems.

Patent Publication 1 shows that with an eye on how the periphery of a screen is seen, distortion control is implemented mainly with lenses. It also shows that distortion is changed by image processing, but it does not take care of how much images on the periphery of the screen are seen by image processing because correction is implemented in the direction of enlarging images on the center and reducing images on the periphery. Although there are no specific lens data, this arrangement unavoidably leads to increases in the size of the optical system: it cannot be used with endoscopes in view of size reductions.

Likewise, Patent Publication 2 pays attention to images on the periphery of the screen, but says nothing specific about lenses or image processing; in other words, it remains to be seen whether that is viable or not.

The prior art set forth in Patent Publications 1 and 2 is used in onboard applications, and has for its object to optimize distortion depending on how it is mounted on a car; that is, it has difficulty in immediate application to endoscopes.

The prior art of Patent Publication 3 is designed such that correction of distortion by image processing is applied to endoscopes. However, the object is to correct images for detection of subjects; so distortion of lenses is merely corrected. Therefore, there is no consideration of how images the periphery are seen at best.

The prior art of Patent Publication 4 uses a changeover switch to, or not to, implement correction of distortion, and is going to be used with cameras. For this reason, when it is used on a wide-angle optical system having large distortion such as that for an endoscope, there is a very large change in images depending on whether or not the correction is implemented, which may rather render viewing very difficult.

These prior arts gain control of distortion, but say nothing about how the complicated morphologies of the inside of the living body are viewed, and about the construction of distortion best suited for viewing through an endoscope as well.

SUMMARY OF THE INVENTION

Having been made with such problems with the prior art in mind, the present invention has for its object to provide an image apparatus for endoscopes that enables the periphery of a screen to be easily viewed while taking the observing angle of view and size into account.

According to a first aspect of the invention, the above object is accomplishable by the provision of an image apparatus for endoscopes, which comprises an optical system adapted to form an optical image of an object, an image pickup device adapted to convert the formed optical image into electric signals to obtain image data, and an image processing means adapted to move and transform a position of the optical image acquired by the image pickup device, wherein a radial direction magnification (meaning the magnification as a function of ray height) is transformable by said image processing means independently from a concentric direction magnification, and a magnification for a conformal object is higher at a peripheral portion than at a center portion of a screen.

The requirements for, and the advantages of, such arrangement of the first aspect are now explained.

When it comes to viewing through a medical endoscope, the organs to be viewed are often in complicated forms; for instance, the operator unavoidably makes an oversight of lesions on the back side or the like of the wall of the large intestine. One possible approach to this end is to increase the angle of view such that images both sideways and backwards with respect to the direction of advancement of the endoscope can be viewed. However, the increased angle of view would cause extreme distortion of the periphery portion of a screen by reason of distortion inherent in optical design. Thus, only with the increased angle of view, lesions cannot be found, making an oversight of lesions is still likely.

According to the invention, therefore, a function of correcting distortion by image processing is attached to an endoscope apparatus thereby correcting distortion.

However, even when a conventional method is immediately applied to an endoscope with a wide-angle optical system mounted on it, it is hard to accomplish the object of the invention. For instance, there has been a way of correcting distortion with a generally ideal image height of $f \cdot \tan \theta$ as a target value. However, as the angle of view $\theta$ becomes 90°, such an ideal image height becomes infinite that is clearly not a proper target value. Further, when the angle of view is greater than 90°, such a target value can no longer be defined. For this reason, such a correction method of using the ideal image height as a reference is not suited for the optical system used here.

Thus, the object to be viewed through the endoscope is a tract and cavity in a stereoscopic rather than planar form, so the optimum distortion correction must be implemented depending on what state viewing takes place in. In viewing a tract and cavity, the operator pays less attention to the center of the screen because light from afar or illumination light does not reach there, and thus the operator pays more attention to the periphery of the screen. At the peripheral portion of the screen, the operator is going to view the lateral surface of the tract and cavity wall, not the surface of the wall perpendicular to the direction of advancement.

Figure 1A:
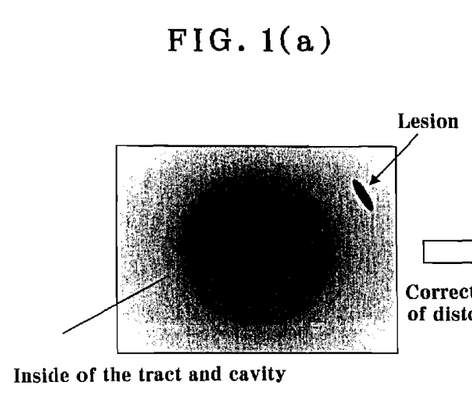
Figure 1B:
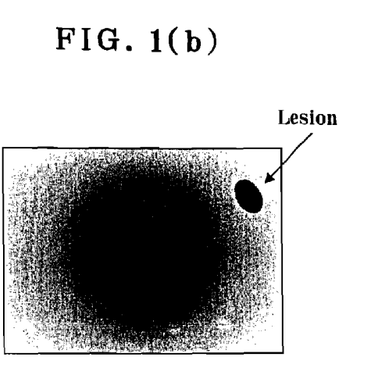
Figure 2:
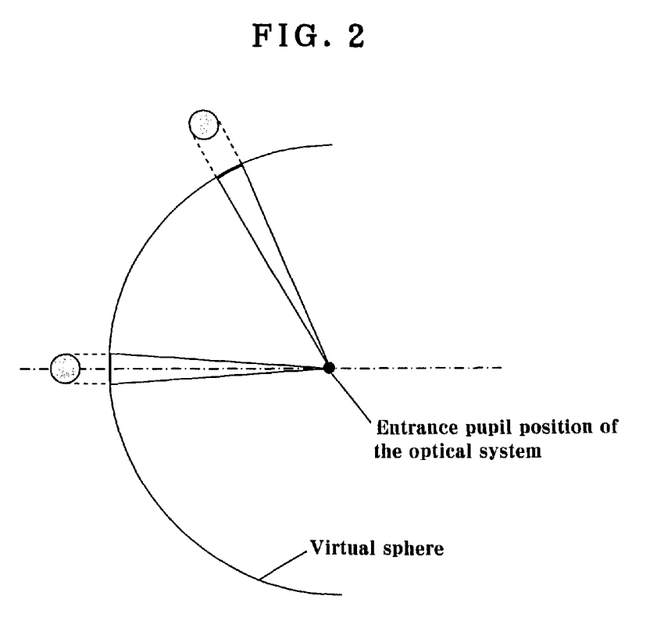
FIG. 2 is illustrative of a conformal object.

In the invention, therefore, the surface of the object to be viewed is presumed to be the spherical internal surface, and distortion correction is optimized on the presumption that there is a minute circle on that internal wall surface. In other words, a magnification for a conformal object in the radial direction is higher at the center than at the periphery of the screen, so that as shown in FIG. 2, a circle indicative of the conformal object at a virtual spherical surface is much the same between the center and the periphery of the screen. This ensures that distortion at the periphery of the screen is corrected and a peripheral portion to which more attention is paid can be seen on an enlarged scale. Thus, as can be seen from the screens before (FIG. 1(*a*)) and (FIG. 1(*b*)) after distortion correction, a lesion in the tract or cavity can easily be viewed; so there is a less possibility of making an oversight of it.

According to a second aspect of the invention, there is an image apparatus for endoscopes provided which comprises an optical system adapted to form an optical image of an object, an image pickup device adapted to convert the formed optical image into electric signals to obtain image data, and an image processing means adapted to move and transform a position of the optical image acquired by the image pickup device, wherein a radial direction magnification is transformable by said image processing means independently from a concentric direction magnification, said radial direction magnification being manually changeable.

The requirements for, and the advantages of, the second aspect of the invention are now explained.

Upon viewing through an endoscope, it is not always possible to view an object surface perpendicular to the field-of-view direction. For instance, upon viewing a narrow space, there is no option but to implement viewing obliquely with respect to the field-of-view direction due to the physical arrangement of an equi-optical apparatus. Such oblique viewing causes the object surface to be seen distorted, unlike direct viewing. This distortion, combined with barrel distortion produced by the optical system, grows larger and larger. This distortion of the object resulting from the angle of viewing depends on operations or object shapes and it cannot be eliminated only by simple correction of the distortion of the optical system.

According to the second aspect of the invention, therefore, the amount of correction of distortion by image processing is manually changeable. By allowing the user to control distortion, distortion of the object caused by the angle of viewing can be corrected depending on the situation involved, making perpendicular viewing possible.

To maximize the advantages of the first and second aspects of the invention, the angle of view of the optical system is of vital importance. It is then preferable to satisfy the following condition (1):

$$70° \leq \theta \leq 150° \quad (1)$$

where $\theta$ is the maximum half angle of view of the optical system.

As the upper limit of 150° to Condition (1) is exceeded, the optical system grows too large for use on an endoscope, even if distortion is corrected by image processing. As the lower limit of 70° is exceeded, the range to be viewed becomes too narrow, failing to take full effect on prevention of making an oversight even if distortion is corrected.

More preferably, the following condition (1-1) should be satisfied.

$$80° \leq \theta \leq 120° \quad (1\text{-}1)$$

Generally with a wide-angle optical system, distortion takes on a barrel form and its peripheral portion is distorted. For this reason, distortion is corrected by image processing in an enlargement direction; so image deterioration due to enlargement processing is unavoidable. In other words, distortion must be controlled at the optical system to some extent. It is then preferable to satisfy the following condition (2).

$$0.5 \leq Ih/(f\cdot\theta) \leq 1.2 \quad (2)$$

where f is a focal length of the optical system, $\theta$ is a maximum half angle of view (in radians), and Ih is a maximum real image height of the optical system.

As the upper limit of 1.2 to Condition (2) is exceeded, it causes overcorrection of distortion of the optical system, only to increase in the number of lenses involved or in the size of the optical system, and as the lower limit of 0.5 is not reached, the amount of correction by image processing grows too large, resulting in image deterioration.

More preferably, the following condition should be satisfied.

$$0.65 \leq Ih/(f\cdot\theta) \leq 0.95 \quad (2)$$

The following condition (3) is preferably satisfied with respect to the magnification of the periphery to the center.

$$0.5 \leq \Delta max/\Delta center \leq 6.0 \quad (3)$$

Here $\Delta max$ and $\Delta center$ are each the magnitude of the conformal object on the image plane: $\Delta center$ is the magnitude of the conformal object at the center of the screen, and $\Delta max$ is the maximum value of the conformal object within the screen.

As the upper limit of 6.0 to Condition (3) is exceeded, display size grows too large, resulting in image deterioration, and as the lower limit of 0.5 is not reached, display size becomes too small for viewing.

More preferably, the following condition should be satisfied.

$$0.8 \leq \Delta max/\Delta center \leq 4.0 \quad (3\text{-}1)$$

Most preferably, the following condition should be satisfied.

$$1.0 \leq \Delta max/\Delta center \leq 3.0 \quad (3\text{-}2)$$

According to the invention, the peripheral portion is enlarged; however, to contain all information within the same display size, the center portion must be reduced relative to the original image. When viewing a simple tract and cavity, on the other hand, its wall surface is seen at an angle of view of 90°; so the object distance becomes shortest and the magnification of the peripheral portion grows naturally high. Thus, the magnification depends on object shape too, and unless the angle of view at that boarder is set right, the image is then hard to see as a whole. Therefore, it is preferable to satisfy the following condition (4) with respect to the angle of view where there is no magnification change.

$$30° \leq \theta fix \leq 90° \quad (4)$$

Here $\theta fix$ is the angle of view where there is no magnification change.

As the upper limit of 90° to Condition (4) is exceeded, the peripheral portion grows overly large, and as the lower limit of 30° is not reached, the center portion becomes overly small.

More preferably, the following condition should be satisfied.

$$40° \leq \theta fix \leq 80° \quad (4\text{-}1)$$

Correction of distortion by image processing involves movement of individual pixels; so the maximum amount of pixel movement has some limits depending on circuit size. It is therefore necessary for the amount of movement to balance distortion of the optical system against circuit design. In other words, it is preferable to satisfy the following condition (5).

$$0 < \Delta / Ih \leq 0.5 \quad (5)$$

Here $\Delta$ is the maximum amount of pixel movement within the screen, and Ih is the maximum image height.

As the upper limit of 0.5 to Condition (5) is exceeded, it causes circuit arrangement to grow huge or processing to delay, throwing an obstacle to viewing, and at the lower limit of 0, the amount of correction becomes too small and the periphery of the screen is seen distorted.

More preferably, the following condition should be satisfied.

$$0.05 < \Delta / Ih \leq 0.35 \quad (5\text{-}1)$$

Upon coordinate transformation by image processing, a transient or intermediate portion of image information obtained at the optical system may possibly be cut; however, it is not preferable because there is a portion incapable of viewing. For this reason, it is preferable that upon coordinate transformation, angle-of-view information is continuously displayed. In other words, it is preferable that at an input to the optical system, a range with continuous angles of view is transformed by one functional polynomial. This ensures that continuity is kept even after transformation.

The coordinate transformation by correction of distortion depends on individual distortions of the optical systems. It is then preferable to hold transformation parameters together with the optical system. It is also desirable that information be stored in a memory or the like built in the apparatus.

Upon correction of barrel distortion, the periphery is extended in a direction of enlargement; so there is an occasion where information on the outermost periphery comes out of the screen. Cutting off the outermost periphery is not preferred because there is a decrease in the substantial angle of view. In other words, it is preferable that optical image information at the maximum angle of view is held before and after transformation.

For instance, when the screen is in a rectangular rather than circular shape, the screen shape is distorted after transformation if the diagonal position of the maximum angle of view remains fixed, resulting in defections. To ease off such defections, therefore, transformation may be implemented such that there is optical image information held at a factor of at least 0.9 of the maximum angle of view.

In general, a wide-angle optical system arrangement is of the retrofocus type. For this reason, more negative power is distributed on an object side with respect to an aperture stop, and more positive power is on an image side. With such arrangement, it gets harder to diminish distortion produced at the optical system. To correct this distortion, there is the need of increasing the number of lenses involved or using aspheric lenses; however, this results in size increases or cost rises. In other words, it is preferable for the optical system to have some distortion left. That is, it is preferable that the conformal object is given optical characteristics such that the magnification of the image is lower at the periphery than at the center.

According to the present invention, it is possible to obtain an image apparatus for endoscopes that enables even an object of complicated shape to be easily viewable.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 1 is illustrative of exemplary screens (a) before and (b) after correction of distortion by the inventive image apparatus for endoscopes.

DESCRIPTION OF THE PREFERRED EMBODIMENTS

The inventive image apparatus for endoscopes is now explained with reference to some examples.

EXAMPLE 1

Figure 3:
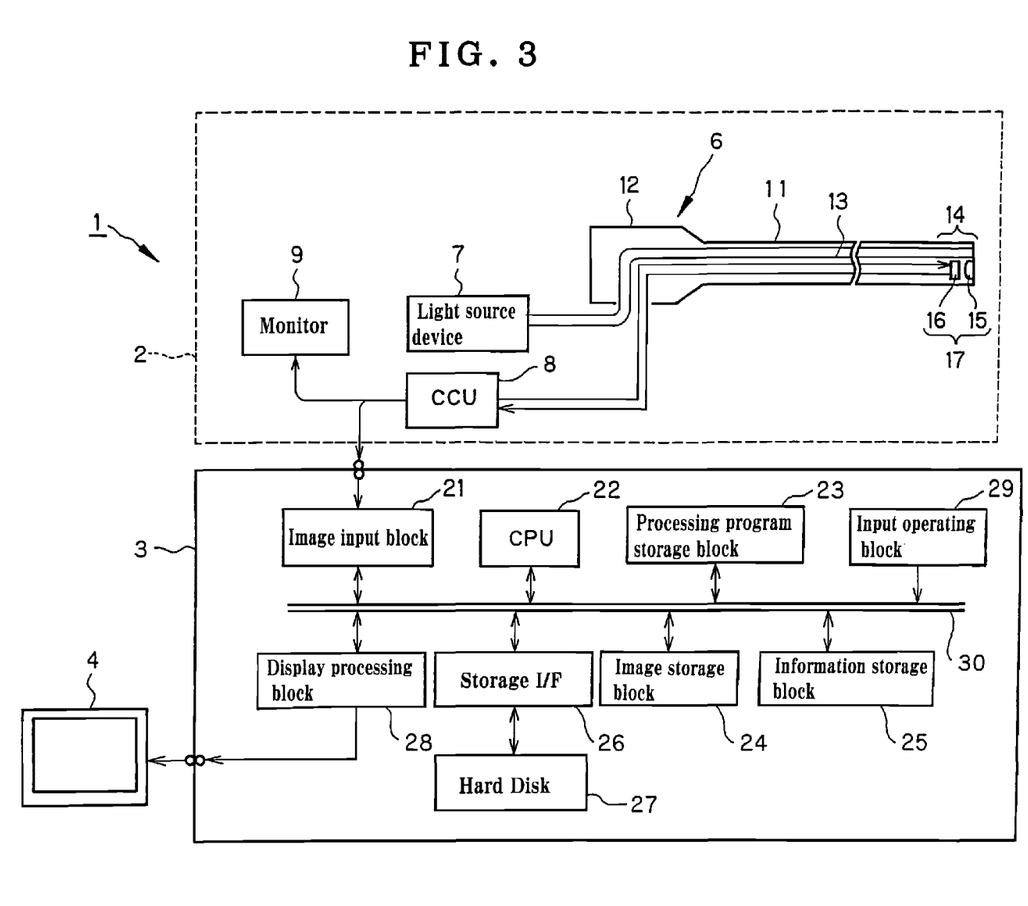
FIG. 3 is a block diagram that shows one arrangement of the inventive endoscope system.

An endoscope system 1 shown in FIG. 3 is built up of an endoscope viewing apparatus 2, a medical image processor (hereinafter referred simply to as the image processor) 3 made up of a personal computer or the like that applies image processing to an endoscope image obtained by the endoscope viewing apparatus 2 as medical information, and a display monitor 4 adapted to display an image processed by the image processor 3.

The endoscope viewing apparatus 2 includes an endoscope 6 inserted through the body, a light source device 7 adapted to feed illumination light to the endoscope 6, a camera control unit (abbreviated as CCU) 8 adapted to apply signal processing to an image pickup means in the endoscope 6, and a monitor 9 in which image signals out of CCU 8 are entered to display an endoscope image taken by the image pickup device 16.

The endoscope 6 includes an insert 11 that is inserted through the body cavity and an operating portion 12 provided at the rear end of the insert 11. The insert 11 has also a light guide 13 passed for transmission of illumination light.

The rear end of the light guide 13 is connected to the light source device 7. And the illumination light supplied from the light source device 7 is transferred through the light guide 13, and leaves an end surface attached to an illumination window provided through a leading end 14 of the insert 11 to illuminate subjects such as affected sites.

Further, there is an image pickup apparatus 17 provided, which is made up of an objective lens 15 attached to a viewing window adjacent to the illumination window and, for instance, a charge coupled device (abbreviated as CCD) 16 that works as a solid-state image pickup device located at an imaging position of the objective lens 15. And an optical image formed on the imaging plane of CCD 16 is subjected to photoelectric transformation at that CCD 16.

The CCD 16 is connected to the CCU 8 via a signal line, and as CCD drive signals are applied from the CCU 8 to the CCD 16, it produces image signals that have undergone photoelectric transformation. The image signals are subjected to signal processing at an image processing circuit in the CCU 8 and transformed into video signals that are in turn sent out to the monitor 9 where an endoscope image is displayed on its display screen. The video signals are also entered in the image processor 3.

The image processor 3 includes an image input block 21 adapted to receive image signals corresponding to the endoscope image entered from the endoscope viewing apparatus 2, a CPU 22 adapted to implement image processing for video signals entered from the image input block 21, and a processing program storage block 23 adapted to store a processing (control) program for letting the CPU 22 run the image processing.

The image processor 3 also includes an image storage block 24 adapted to store image data or the like entered from the image input block 21, an information storage block 25 adapted to store information processed by the CPU 22, a hard disk 26 that works as a storage for storing the image data, information, etc. processed by the CPU 22 via a storage interface 26, a display processing block 28 adapted to implement display processing for displaying the image data or the like processed by the CPU 22, and an input operating block 29 comprising a keyboard through which the user enters data such as image processing parameters and instructions. The video signals generated by the display processing block 28 are displayed on the display monitor 4, and the processed image is displayed on the display plane of the display monitor 4.

It is here noted that the image input block 21, CPU 22, processing program storage block 23, image storage block 24, information storage block 25, storage interface 26, display processing block 28 and input operating block 29 are interconnected together via a data bus 30.

Figure 4:
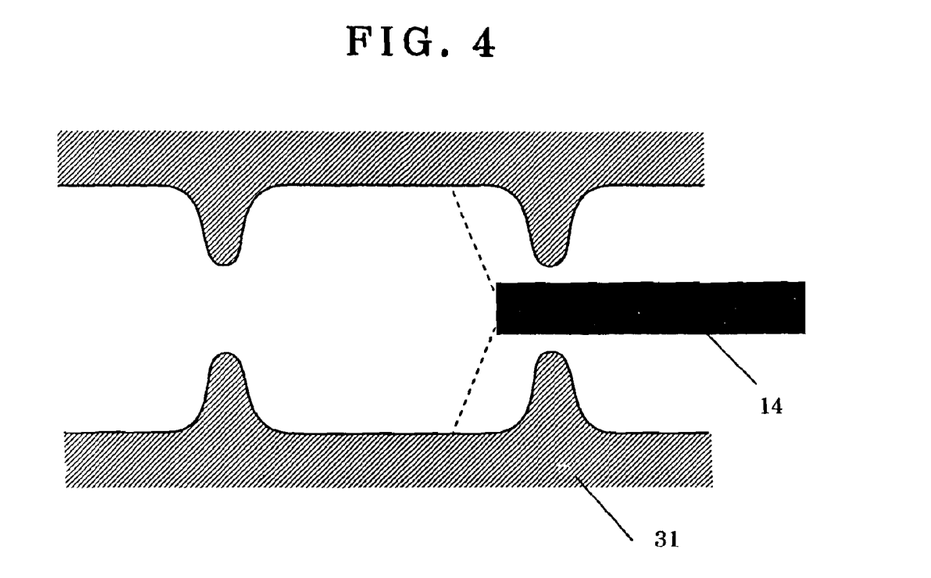
FIG. 4 is illustrative of one exemplary viewing of the large intestine through an endoscope.

In the example here, the insert 11 of the direct-view type endoscope 6 is inserted through a tract site (tract organ) like the large intestine 31, as shown in FIG. 4, and images of that site are taken by the image pickup device 17 at the leading end 14 Note that the objective lens 15 here is constructed as follows.

Figure 6:
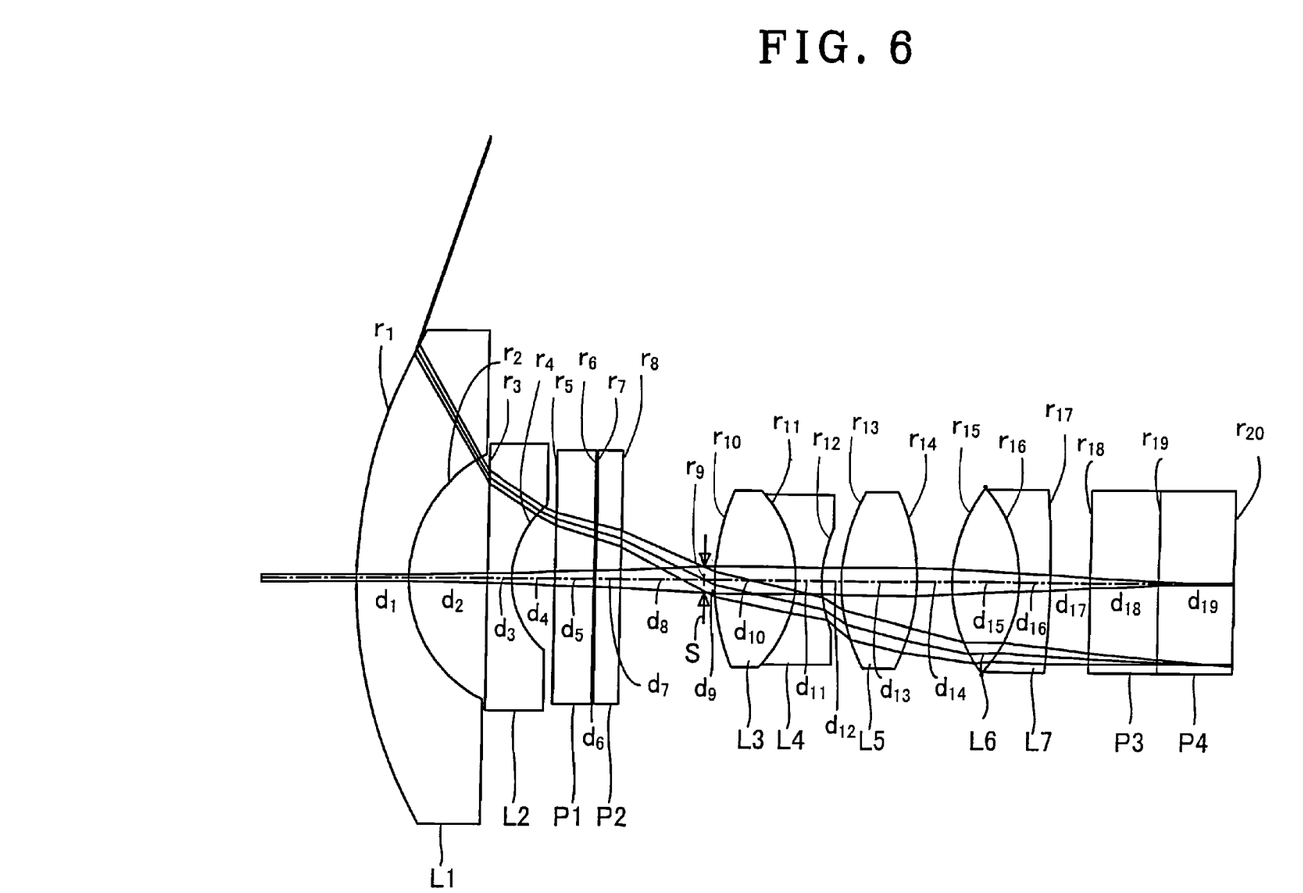
FIG. 6 is illustrative in lens arrangement section of the objective lens used in Example 1, 2, and 3.

FIG. 6 is illustrative in lens arrangement section of the objective lens 15. As shown there, the objective lens is made up of, in order from its object side, a first negative meniscus lens L1 convex on its object side, a second negative lens L2 that is planar on its object side, a parallel-plane plate P1, a parallel-plane plate P2, an aperture stop S, a third positive lens L3 of double-convex shape, a fourth negative lens L4 of double-concave shape, a fifth positive lens L5 of double-convex shape, a sixth positive lens L6 of double-convex shape, a seventh negative meniscus lens L7 convex on its image side, a parallel-plane plate P3, and a parallel-plane plate P4. The third positive lens L3 and the fourth negative lens L4, and the sixth positive lens L6 and the seventh negative lens L7 are cemented together, respectively. The specifications of the example here are directed to a wide-angle optical system having a focal length of 0.865 mm, a maximum image height of 1.31 mm and a half angle of view of 108.6°.

Numerical data on the lens system of the example here will be tabulated later. In the tables, the surface number of an optical surface as counted from the object side is indicated by "No.", the radius of curvature by "r", a surface-to-surface space or an air space by "d", a d-line refractive index by "nd", and an Abbe constant by "vd", respectively. The radius of curvature and the surface-to-surface space are given in mm.

In conjunction with FIG. 6, it is noted that optical surfaces with Surface Nos. 1, 2, 3, ... are indicated by $r_1, r_2, r_3, \ldots$, and the spaces or air spaces between Surface Nos. 1 and 2, Surface Nos. 2 and 3, Surface Nos. 3 and 4, ... are indicated by $d_1, d_2, d_3, \ldots$.

How the endoscope system 1 works is now explained. First, the user puts on the power sources of the blocks that the endoscope system 1 has, and then inserts the insert 11 of the endoscope 6 through the body cavity of a subject.

And as the insert 11 is inserted by the user through the subject's body cavity, images of objects, for instance, biological tissues existing there are taken by the image pickup apparatus 17 attached to the leading end 14. And the object images taken by the image pickup apparatus 17 are sent as imaging signals out to the CCU B.

In the CCU 8, signal processing is applied at a signal processing circuit (not shown) to imaging signals out of the image pickup device 16 in the image pickup apparatus 17, thereby transforming those imaging signals into video signals for a two-dimensional image and sending out them to the medical image processor 3.

After the video signals for a two-dimensional image sent out to the medical image processor 3 are A/D transformed at the image input block 21, they are entered in the CPU 22 at which distortion of the two-dimensional image out of the image input block 21 is corrected.

Figure 5:
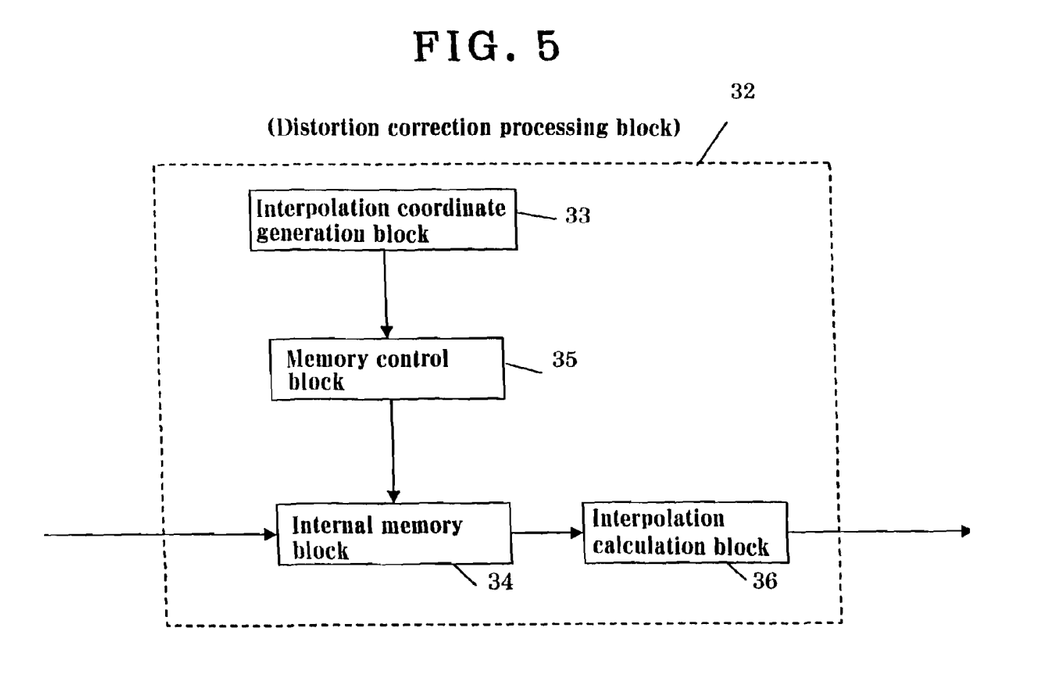
FIG. 5 is a block diagram that shows one exemplary arrangement of the distortion correction block.

As shown in FIG. 5, a distortion correction block 32 is comprised of an interpolation coordinates generation block 33 adapted to generate a position of an image whose distortion has been corrected (referred to as the interpolation position: (X, Y)) and a position of the associated original image whose distortion is not yet corrected (X', Y'), an internal memory block 34 that works as a buffer memory adapted to temporarily store a part of the image data from a circuit in the pre-block of the distortion correction block 32, a memory control block 35 adapted to implement control of writing on and reading from that internal memory block 34, and an interpolation computation block 36 adapted to implement image processing according to the coordinates (X', Y') of the transformed image position before the application of distortion correction.

The interpolation coordinates generation block 33 produces an output of the before-correction coordinates (X', Y') transformed by the application of a given distortion correction formula to the coordinates (X, Y). In the example here, transformation is implemented in terms of the following functional formulae.

$$X' = (m \cdot X) \cdot (1 + a \cdot Z^2 + b \cdot Z^4 + c \cdot Z^6)$$

$$Y' = (m \cdot Y) \cdot (1 + a \cdot Z^2 + b \cdot Z^4 + c \cdot Z^6)$$

Here, $Z^2 = (m \cdot X)^2 + (m \cdot y)^2$, and m, a, b and c are parameters.

In the example here, X and Y are normalized such that the maximum value of Z becomes 1, and the coefficients are set at m=1.74103, a=−0.25250, b=0.03235, and c=0.00169, respectively, and such that the maximum image height position remains fixed before and after transformation.

Figure 7:
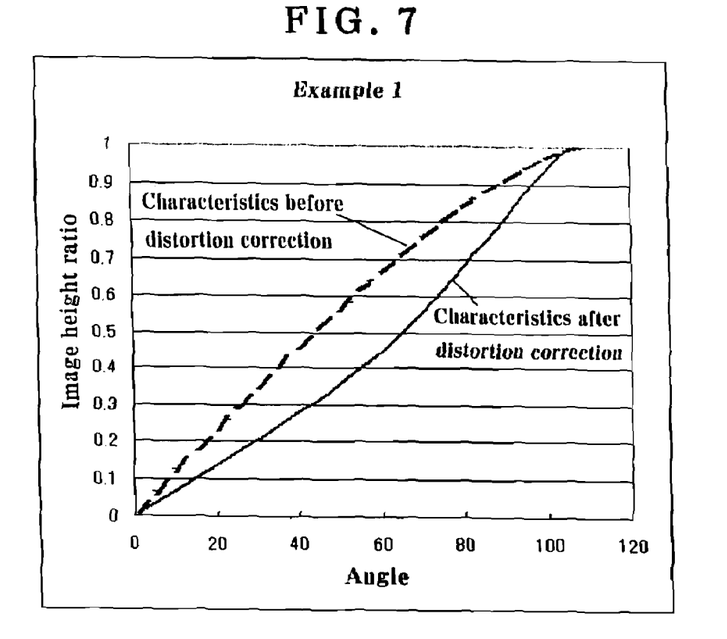
FIG. 7 is illustrative of image height ratio versus angle-of-view characteristics in Example 1.

The image height ration versus angle-of-view characteristics in Example 1 are presented in FIG. 7. In a state where there is no distortion correction applied, that is, with distortion characteristics of the optical system alone, as the angle of view increases, it causes the change in the image height ratio to decrease, and objects to be seen distorted. By implementing the above distortion correction, the magnification of the peripheral portion to the center portion of the screen is extended so that distortion is ameliorated to make objects easily viewable.

A control button for distortion correction is located in the input operating block 29. The endoscope 6 has a plurality of distortion correction parameters registered and stored in the memory beforehand. If the user pushes down that button, it is then possible to call out the stored parameters and phase the degree of distortion, thereby displaying on the monitor 4 an image in which distortion at the periphery of the screen is corrected.

EXAMPLE 2

Example 2 is much the same in arrangement as Example 1 with the exception that the distortion parameters are changed.

In the example here, the coefficients are set at m=1.19568, a=0.13243, b=−0.42603, and c=0.17871, respectively.

Figure 8:
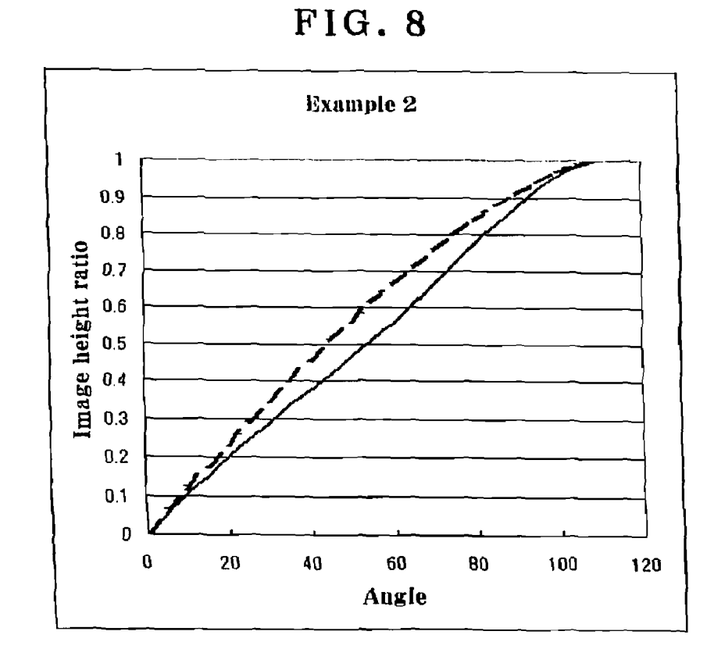
FIG. 8 is illustrative of image height ratio versus angle-of-view characteristics in Example 2.

The image height ratio characteristics with respect to the angle of view in Example 2 are presented in FIG. 8 (what is meant by the curve in FIG. 7 also goes for the curve here).

EXAMPLE 3

Example 3 is much the same in arrangement as Example 1 with the exception that the distortion parameters are changed.

In the example here, the coefficients are set at m=1.91587, a=−0.44743, b=0.15274, and c=−0.01816, respectively.

Figure 9:
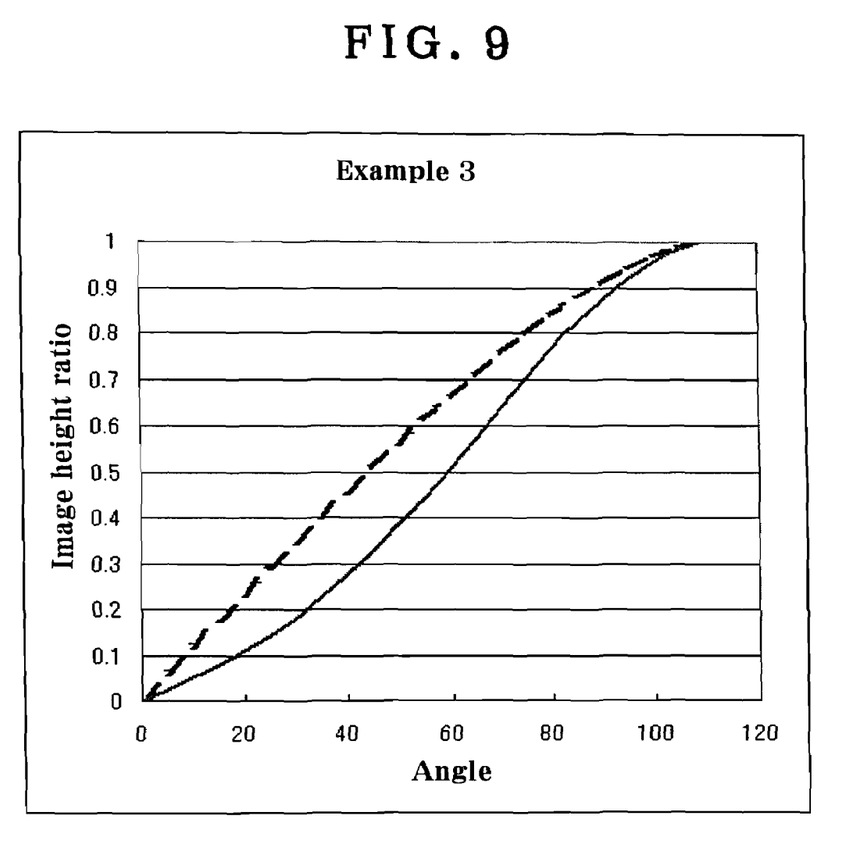
FIG. 9 is illustrative of image height ratio versus angle-of-view characteristics in Example 3.

The image height ratio characteristics with respect to the angle of view in Example 3 are presented in FIG. 9 (what is meant by the curve in FIG. 7 also goes for the curve here).

EXAMPLE 4

Figure 10:
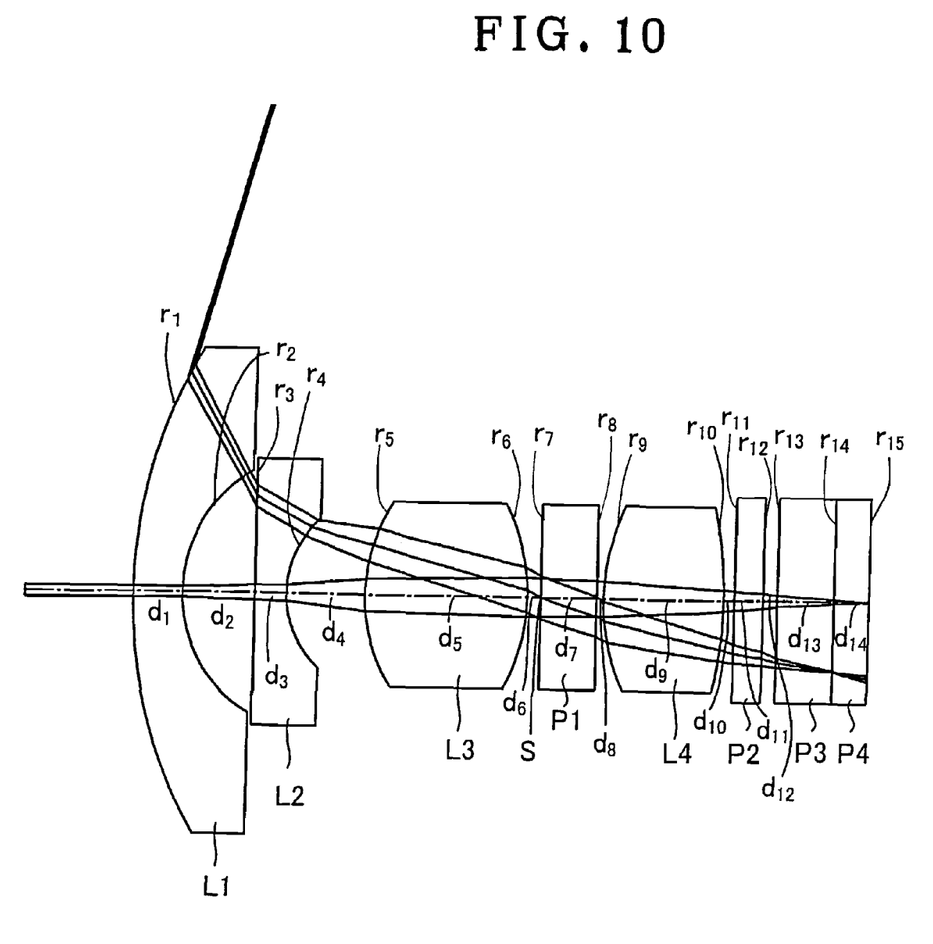
FIG. 10 is illustrative in lens arrangement section of the objective lens used in Example 4, and 5.

Example 4 is much the same in arrangement as Example 1 with the exception that the optical parameters of the objective lens 15 are changed.

FIG. 10 is illustrative in lens arrangement section of the objective lens 15 here. As shown there, the objective lens 15 is made up of, in order from its object side, a first negative meniscus lens L1 convex on its object side, a second negative lens L2 that is planar on its object side, a third positive lens L3 of double-convex shape, an aperture stop S, a parallel-plane plate P1, a fourth positive lens L4 of double-convex shape, a parallel-plane plate P2, a parallel-plane plate P3 and a parallel-plane plate P4. The parallel-plane plates P3 and P4 are cemented together, and the aperture stop S is positioned on the front surface of the parallel-plane plate P1. The specifications of the example here are directed to a wide-angle optical system having a focal length of 0.698 mm, a maximum image height of 1.04 mm and a half angle of view of 106.0°.

Numerical data on the lens system of the example here will be tabulated later. In the tables, the surface number of an optical surface as counted from the object side is indicated by "No.", the radius of curvature by "r", a surface-to-surface space or an air space by "d", a d-line refractive index by "nd", and an Abbe constant by "vd", respectively. The radius of curvature and the surface-to-surface space are given in mm.

In conjunction with FIG. 10, it is noted that optical surfaces with Surface Nos. 1, 2, 3, . . . are indicated by $r_1, r_2, r_3, \ldots$, and the spaces or air spaces between Surface Nos. 1 and 2, Surface Nos. 2 and 3, Surface Nos. 3 and 4, . . . are indicated by $d_1, d_2, d_3$, In the example here, the optical system and the distortion parameters are modified or changed.

In the example here, the coefficients are set at m=1.32694, a=0.43797, b=−0.71164, and c=0.21812, respectively.

Figure 11:
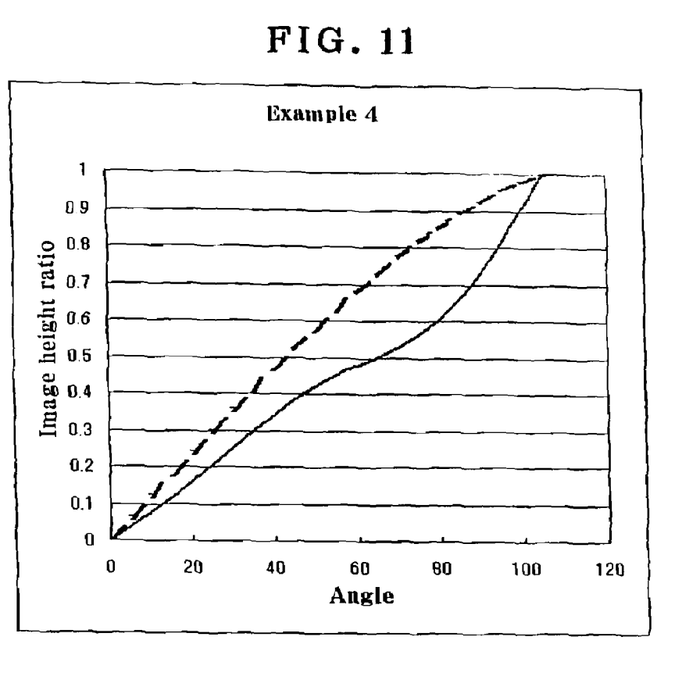
FIG. 11 is illustrative of image height ratio versus angle-of-view characteristics in Example 4.

The image height ratio characteristics with respect to the angle of view in Example 4 are presented in FIG. 11 (what is meant by the curve in FIG. 7 goes for the curve here, too).

EXAMPLE 5

Example 5 is much the same in arrangement as Example 4 with the exception that the distortion parameters are changed.

In the example here, the coefficients are set at m=2.23601, a=−0.31206, b=0.06487, and c=−0.00491, respectively.

Figure 12:
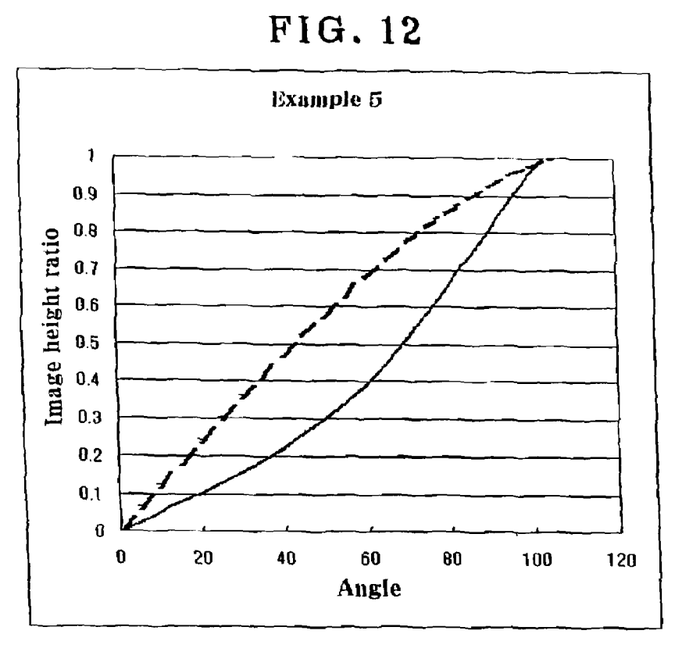
FIG. 12 is illustrative of image height ratio versus angle-of-view characteristics in Example 5.

The image height ratio characteristics with respect to the angle of view in Example 3 are presented in FIG. 12 (what is meant by the curve in FIG. 7 also goes for the curve here).

Tabulated below are numerical data on the objective lens 15 used in Examples 1 to 5. Example 2 and 3 are the same as Example 1, and Example 5 is the same as Example 4: there are the numerical data on Examples 1 and 4 given below.

Note here that f is a focal length and ω is a half angle of view.

EXAMPLE 1

| No | r | d | nd | vd |
|---|---|---|---|---|
| 1 | 7.8797 | 0.813 | 1.88300 | 40.76 |
| 2 | 2.1240 | 1.283 | | |
| 3 | ∞ | 0.400 | 1.56883 | 56.36 |
| 4 | 1.4928 | 0.700 | | |
| 5 | ∞ | 0.620 | 1.51400 | 75.00 |
| 6 | ∞ | 0.030 | | |
| 7 | ∞ | 0.400 | 1.52287 | 59.89 |
| 8 | ∞ | 1.363 | | |
| 9 (Stop) | ∞ | 0.170 | | |
| 10 | 3.6072 | 1.291 | 1.88300 | 40.76 |
| 11 | −2.0000 | 0.418 | 1.72151 | 29.23 |
| 12 | 2.0933 | 0.319 | | |
| 13 | 2.7967 | 1.252 | 1.56883 | 56.36 |
| 14 | −3.0527 | 0.566 | | |
| 15 | 2.4330 | 1.072 | 1.51633 | 64.14 |
| 16 | −2.1514 | 0.500 | 1.84666 | 23.78 |
| 17 | −16.5531 | 0.648 | | |
| 18 | ∞ | 1.130 | 1.51633 | 64.14 |
| 19 | ∞ | 1.230 | 1.51633 | 64.14 |
| 20 | ∞ | | | |
| f | 0.865 | | | |
| FNO. | 7.50 | | | |
| ω | 108.6° | | | |

EXAMPLE 4

| No | r | d | nd | vd |
|---|---|---|---|---|
| 1 | 6.3338 | 0.695 | 1.88300 | 40.78 |
| 2 | 1.8420 | 1.032 | | |
| 3 | ∞ | 0.450 | 1.88300 | 40.78 |
| 4 | 1.2952 | 1.123 | | |
| 5 | 2.2201 | 2.282 | 1.64769 | 33.79 |
| 6 | −2.6039 | 0.190 | | |
| 7 (Stop) | ∞ | 0.795 | 1.51400 | 75.00 |
| 8 | ∞ | 0.100 | | |
| 9 | 2.7732 | 1.725 | 1.71999 | 50.22 |
| 10 | −5.1958 | 0.150 | | |
| 11 | ∞ | 0.400 | 1.88300 | 40.78 |
| 12 | ∞ | 0.200 | | |
| 13 | ∞ | 0.800 | 1.88300 | 40.78 |
| 14 | ∞ | 0.500 | 1.48749 | 70.21 |
| 15 | ∞ | | | |
| f | 0.698 | | | |
| FNO. | 4.75 | | | |
| ω | 106.0° | | | |

Although the optical system of each of the above examples is embodied as a fisheye lens having a half angle of view of greater than 90°, it is acceptable to apply it to a wide-angle optical system having a narrower angle of view. A lens of meniscus shape convex on its object side may be used as the second negative lens in the optical system of every one of the above examples.

It is noted that the functional formula for implementing distortion correction may be defined in any desired way, and an eighth-, tenth-order formula or the like may be used for it.

The level of correction of distortion by the user may have phases or none. The user may operate the image apparatus by buttons or volume buttons, and operating switches may be located at the image processor 3 or the endoscope 6.

Figure 13A:
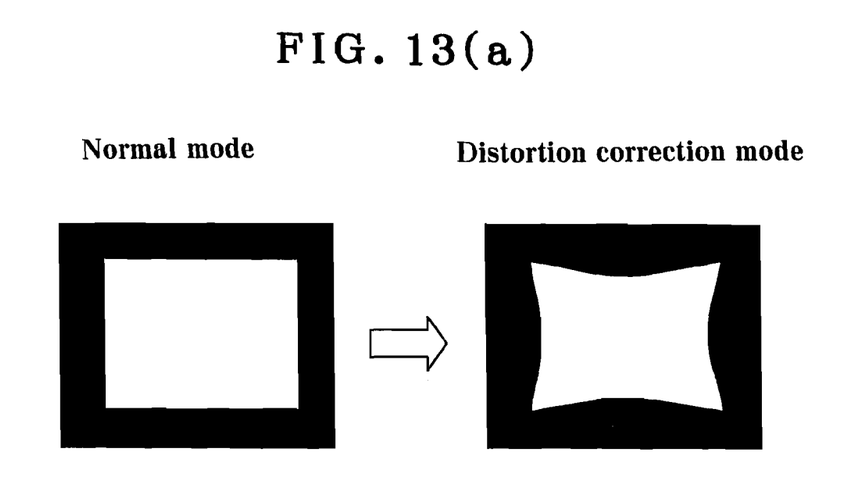
FIG. 13 is illustrative of an example wherein a field-of-view range is enlarged and displayed beforehand to keep it in a rectangular form on the basis of the invention.

It is here noted that image pickup devices such as CCDs are generally in rectangular form, and so when displacements in the radiation direction are added to that, it is impossible to keep the field-of-view range in rectangular form. That is, as shown in FIG. 13(a), a rectangular line is distorted into a reel form. With the non-rectangular field of view, there seems to be deficiencies that make it difficult for the viewer to see.

Figure 13B:
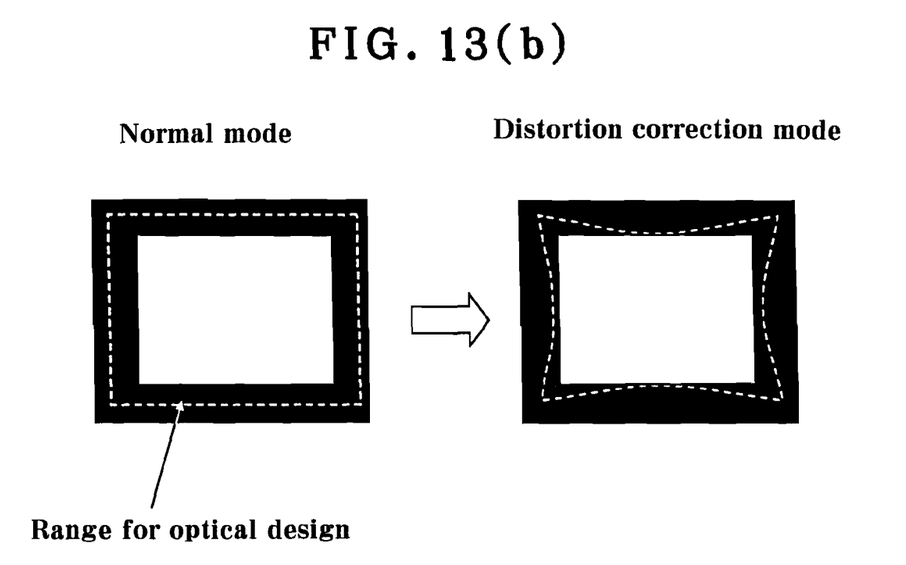

Therefore, as shown in FIG. 13(b), it is preferable to enlarge and display images in a normal mode such that there is no deficiency even with correction of distortion. If this is done, it is then possible to prevent the occurrence of deficiencies at the time of distortion correction. It is then desired that the optical system be designed to have a large angle of view such that the necessary angle of view is indicated in the normal mode.

Tabulated below are the values of Conditions (1) to (5) in the respective examples.

| | Ex. 1 | Ex. 2 | Ex. 3 | Ex. 4 | Ex. 5 |
|---|---|---|---|---|---|
| (1) θ | 108.6 | 108.6 | 108.6 | 106 | 106 |
| (2) Ih/(f·θ) | 0.795 | 0.795 | 0.795 | 0.780 | 0.780 |
| (3) Δmax/Δcenter | 1.971 | 1.087 | 2.696 | 2.373 | 3.585 |
| θfix | 58 | 58 | 43 | 76 | 57 |
| Δ/Ih | 0.215 | 0.105 | 0.184 | 0.250 | 0.284 |

Further, the present invention may be embodied as follows.

[1] An image apparatus for endoscopes, which comprises an optical system adapted to form an optical image of an object, an image pickup device adapted to convert the formed optical image into electric signals to obtain image data, and an image processing means adapted to move and transform a position of the optical image acquired by the image pickup device, wherein a radiation direction magnification is transformable by said image processing means independently from a concentric direction magnification, and a magnification for a conformal object is higher at a peripheral portion than at a central portion of a screen.

[2] An image apparatus for endoscopes, comprising an optical system adapted to form an optical image of an object, an image pickup device adapted to convert the formed optical image into electric signals to obtain image data, and an image processing means adapted to move and transform a position of the optical image acquired by the image pickup device, wherein a radiation direction magnification is transformable by said imaging processing means independently from a concentric direction magnification, and there is a switch means capable of changing said radiation direction magnification in manual operation.

I claim:

1. An image apparatus for endoscopes, comprising:
   an optical system adapted to form an optical image of an object,
   an image pickup device adapted to convert the formed optical image into electric signals to obtain image data, and
   an image processing means adapted to move and transform a position of the optical image acquired by the image pickup device, characterized in that a radial direction magnification is transformable by said image processing means independently from a concentric direction magnification, and a magnification for a conformal object is higher at a peripheral portion than at a central portion of a screen.

2. An image apparatus for endoscopes comprising:
   an optical system adapted to form an optical image of an object,
   an image pickup device adapted to convert the formed optical image into electric signals to obtain image data, and
   an image processing means adapted to move and transform a position of the optical image acquired by the image pickup device, characterized in that a radial direction magnification is transformable by said image processing means independently from a concentric direction magnification, said radial direction magnification being manually changeable.

3. The image apparatus for endoscopes according to claim 1, characterized in that said optical system satisfies the following condition (1):

$$70° \leq \theta \leq 150° \tag{1}$$

where
   θ is a maximum half angle of view of the optical system.

4. The image apparatus for endoscopes according to claim 1, characterized in that said optical system satisfies the following condition (2):

$$0.5 \leq Ih/(f\theta) \leq 1.2 \tag{2}$$

where
   f is a focal length of the optical system,
   θ is a maximum half angle of view (in radians), and
   Ih is a maximum real image height of the optical system.

5. The image apparatus for endoscopes according to claim 1, characterized in that a magnification of periphery to center satisfies the following condition (3):

$$0.5 \leq \Delta max/\Delta center \leq 6.0 \quad (3)$$

where

Δmax and Δcenter are each a magnitude of the conformal object magnification on an image plane, with Δcenter being the magnitude of the conformal object at a center of a screen, and Δmax being the maximum value of the conformal object magnification within the screen.

6. The image apparatus for endoscopes according to claim 1, characterized in that an angle of view where there is no magnification change satisfies the following condition (4):

$$30° \leq \theta fix \leq 90° \quad (4)$$

where

θfix is the angle of view where there is no magnification change.

7. The image apparatus for endoscopes according to claim 1, characterized in that a maximum amount of pixel movement satisfies the following condition (5):

$$0 \leq \Delta/Ih \leq 0.5 \quad (5)$$

where

Δ is a maximum amount of pixel movement within the screen, and

Ih is a maximum image height.

8. The image apparatus for endoscopes according to claim 1, characterized in that, in a range where there is a continuous input angle of view provided by said optical system, coordinate transformation by image processing uses one functional polynomial.

9. The image apparatus for endoscopes according to claim 1, characterized in that coordinate transformation for the optical image uses a functional polynomial with its parameters stored in the apparatus beforehand.

10. The image apparatus for endoscopes according to claim 1, characterized in that optical information at a maximum angle of view is held before and after coordinate transformation.

11. The image apparatus for endoscopes according to claim 1, characterized in that optical information at a factor of at least 0.9 of a maximum angle of view is held before and after coordinate transformation.

12. The image apparatus for endoscopes according to claim 1, characterized in that said optical system has distortion characteristics such that a magnification is lower at a periphery than at a center of the conformal object.

13. The image apparatus for endoscopes according to claim 2, characterized in that said optical system satisfies the following condition (1):

$$70° \leq \theta \leq 150° \quad (1)$$

where

θ is a maximum half angle of view of the optical system.

14. The image apparatus for endoscopes according to claim 2, characterized in that said optical system satisfies the following condition (2):

$$0.5 \leq Ih/(f \cdot \theta) \leq 1.2 \quad (2)$$

where f is a focal length of the optical system,

θ is a maximum half angle of view (in radians), and

Ih is a maximum real image height of the optical system.

15. The image apparatus for endoscopes according to claim 2, characterized in that a magnification of periphery to center satisfies the following condition (3):

$$0.5 \leq \Delta max/\Delta center \leq 6.0 \quad (3)$$

where

Δmax and Δcenter are each a magnitude of the conformal object magnification on an image plane, with Δcenter being the magnitude of the conformal object at a center of a screen, and Δmax being the maximum value of the conformal object magnitude within the screen.

16. The image apparatus for endoscopes according to claim 2, characterized in that an angle of view where there is no magnification change satisfies the following condition (4):

$$30° \leq \theta fix \leq 90° \quad (4)$$

where

θfix is the angle of view where there is no magnification change.

17. The image apparatus for endoscopes according to claim 2, characterized in that a maximum amount of pixel movement satisfies the following condition (5):

$$0 \leq \Delta/Ih \leq 0.5 \quad (5)$$

where

Δ is a maximum amount of pixel movement within the screen, and

Ih is a maximum image height.

18. The image apparatus for endoscopes according to claim 2, characterized in that, in a range where there is a continuous input angle of view provided by said optical system, coordinate transformation by image processing uses one functional polynomial.

19. The image apparatus for endoscopes according to claim 2, characterized in that coordinate transformation for the optical image uses a functional polynomial with its parameters stored in the apparatus beforehand.

20. The image apparatus for endoscopes according to claim 2, characterized in that optical information at a maximum angle of view is held before and after coordinate transformation.

21. The image apparatus for endoscopes according to claim 2, characterized in that optical information at a factor of at least 0.9 of a maximum angle of view is held before and after coordinate transformation.

22. The image apparatus for endoscopes according to claim 1, characterized in that said optical system has distortion characteristics such that a magnification is lower at a periphery than at a center of the conformal object.

23. An image apparatus for endoscopes comprising;

an optical system adapted to form an optical image of an object, an image pickup device adapted to convert the formed optical image into electric signals to obtain image data, and an image processing means adapted to move and transform a position of the optical image acquired by the image pickup device, wherein a radial direction magnification is transformable by said image processing means independently from a concentric direction magnification, and a magnification for a conformal object is higher at a peripheral portion than at a central portion of a screen.

24. An image apparatus for endoscopes, comprising:

an optical system adapted to form an optical image of an object, an image pickup device adapted to convert the formed optical image into electric signals to obtain image data, and an image processing means adapted to move and transform a position of the optical image acquired by the image pickup device, wherein a radial direction magnification is transformable by said imaging processing means independently from a concentric direction magnification, and there is a switch means capable of changing said radial direction magnification in manual operation.

\* \* \* \* \*

UNITED STATES PATENT AND TRADEMARK OFFICE
CERTIFICATE OF CORRECTION

| | | |
|---|---|---|
| PATENT NO. | : 8,647,260 B2 | Page 1 of 1 |
| APPLICATION NO. | : 12/434464 | |
| DATED | : February 11, 2014 | |
| INVENTOR(S) | : Kamo | |

It is certified that error appears in the above-identified patent and that said Letters Patent is hereby corrected as shown below:

On the Title Page, Item (56) the list of Foreign Patent Documents listed on the front page should include the following four additional documents:

| | | |
|---|---|---|
| JP | 2005-110207 A | 4/2005 |
| JP | 2007-038856 A | 2/2007 |
| JP | 2007-124088 A | 5/2007 |
| JP | H-11-275444 A | 10/1999 |

Signed and Sealed this
Twenty-seventh Day of May, 2014

Michelle K. Lee
*Deputy Director of the United States Patent and Trademark Office*